(12) United States Patent
Yayon et al.

(10) Patent No.: US 8,298,528 B2
(45) Date of Patent: Oct. 30, 2012

(54) METHODS FOR BONE REGENERATION USING ENDOTHELIAL PROGENITOR CELL PREPARATIONS

(75) Inventors: Avner Yayon, Moshav Sitria (IL); Dina Lewinson, Zichron Ya'akov (IL); Nimrod Rozen, Haifa (IL)

(73) Assignee: Hepacore Ltd., Ness Ziona (IL)

( * ) Notice: Subject to any disclaimer, the term of this patent is extended or adjusted under 35 U.S.C. 154(b) by 735 days.

(21) Appl. No.: 12/297,417

(22) PCT Filed: Apr. 17, 2007

(86) PCT No.: PCT/IL2007/000485
§ 371 (c)(1),
(2), (4) Date: Feb. 4, 2009

(87) PCT Pub. No.: WO2007/119240
PCT Pub. Date: Oct. 25, 2007

(65) Prior Publication Data
US 2010/0003222 A1 Jan. 7, 2010

Related U.S. Application Data

(60) Provisional application No. 60/792,341, filed on Apr. 17, 2006.

(51) Int. Cl.
 A01N 63/00 (2006.01)
 A61K 48/00 (2006.01)
 C12N 5/00 (2006.01)
(52) U.S. Cl. .................. 424/93.7; 424/93.1; 435/325
(58) Field of Classification Search .............. 424/93.7, 424/93.1; 435/325
See application file for complete search history.

(56) References Cited

U.S. PATENT DOCUMENTS

| | | | |
|---|---|---|---|
| 4,296,100 A | 10/1981 | Franco | 424/108 |
| 4,378,347 A | 3/1983 | Franco | 424/108 |
| 4,880,610 A | 11/1989 | Constanz | 423/305 |
| 4,950,483 A | 8/1990 | Ksander et al. | 424/422 |
| 5,614,496 A | 3/1997 | Dunstan et al. | 514/12 |
| 5,650,176 A | 7/1997 | Lee et al. | 424/602 |
| 5,656,598 A | 8/1997 | Dunstan et al. | 514/12 |
| 5,676,976 A | 10/1997 | Lee et al. | 424/602 |
| 5,683,461 A | 11/1997 | Lee et al. | 623/16 |
| 5,811,094 A | 9/1998 | Caplan et al. | 424/93.7 |
| 5,859,208 A | 1/1999 | Fiddes et al. | 530/399 |
| 5,972,703 A | 10/1999 | Long et al. | 435/372 |
| 6,294,359 B1 | 9/2001 | Fiddes et al. | 435/69.4 |
| 6,352,971 B1 | 3/2002 | Deisher et al. | 514/2 |
| 6,355,239 B1 | 3/2002 | Bruder et al. | 424/93.1 |
| 6,541,024 B1 | 4/2003 | Kadiyala et al. | 424/426 |
| 6,720,340 B1 | 4/2004 | Cooke et al. | 514/343 |
| 6,863,900 B2 | 3/2005 | Kadiyala et al. | 424/426 |
| 6,878,371 B2 | 4/2005 | Ueno et al. | 424/93.1 |
| 7,009,039 B2 | 3/2006 | Yayon et al. | 530/381 |
| 7,029,666 B2 | 4/2006 | Bruder et al. | 424/93.1 |
| 2003/0161817 A1 | 8/2003 | Young et al. | 424/93.21 |
| 2003/0232050 A1 | 12/2003 | Isner et al. | 424/144.1 |
| 2005/0048644 A1 | 3/2005 | Hedrick et al. | 435/289.1 |

FOREIGN PATENT DOCUMENTS

| | | |
|---|---|---|
| WO | WO 00/47130 | 8/2000 |
| WO | WO 02/36732 | 5/2002 |
| WO | WO 03/094835 | 11/2003 |
| WO | WO 2004/028580 * | 5/2004 |
| WO | WO 2004/043333 A2 | 5/2004 |
| WO | WO 2004/067704 | 8/2004 |
| WO | WO 2004/084950 A2 | 10/2004 |
| WO | WO 2005/120090 A2 | 12/2005 |
| WO | WO 2006/008748 | 1/2006 |

OTHER PUBLICATIONS

Ingram et al. (Blood, 104: 2752-2760, 2004).*
Asahara, T. et al., "Isolation of putative progenitor endothelial cells for angiogenesis", Science, vol. 275, pp. 964-967, (1997).
Bancroft, G. N. et al., "Bone tissue engineering by cell transplantation", Eds. Ikada Y., Oshima N., Tissue engineering for therapeutic use 5, Elsevier, pp. 151-163, (2001).
Bellik, L. et al., "Morphological and phenotypical characterization of human endothelial progenitor cells in an early stage of differentiation", FEBS Letters, vol. 579, pp. 2731-2736, (2005).
Bruder, S. P. et al., "Growth kinetics, self-renewal, and the osteogenic potential of purified human mesenchymal stem cells during extensive subcultivation and following cryopreservation", J. Cell. Biochem., vol. 64, pp. 278-294, (1997).
Cetrulo, C. L. Jr. et al., "Stem cells and distraction osteogenesis: endothelial progenitor cells home to the ischemic generate in activation and consolidation", Plastic and Reconstructive Surgery, vol. 116, pp. 1053-1064, (2005).
Connolly, J. F. et al., "Autologous marrow injection as a substitute for operative grafting of tibial non-unions", Clinical Orthopaedics and Related Research, vol. 266, pp. 259-270, (1991).
Doyle, B. et al., "Endothelial progenitor cells", Endothelium, vol. 13, pp. 403-410, (2006).
Flamme, I. et al., "Induction of vasculogenesis and hematopoiesis in vitro", Development, vol. 116, pp. 435-439, (1992).
Hatzopoulos, A. K. et al., "Isolation and characterization of endothelial progenitor cells from mouse embryos", Development, vol. 125, pp. 1457-1468, (1998).
Humpert, P.M. et al., "Locally applied mononuclear bone marrow cells restore angiogenesis and promote wound healing in a type 2 diabetic patient", Exp. Clin. Endocrinol Diabetes, vol. 113, pp. 538-540, (2005).
Hunting, C.B. et al., "Circulating endothelial (progenitor) cells reflect the state of the endothelium: vascular injury, repair and neovascularization", Vox Sanguinis, vol. 88, pp. 1-9, (2005).
Ingram, D. A. et al., "Identification of a novel hierarchy of endothelial progenitor cells using human peripheral and umbilical cord blood", Blood, vol. 104, No. 9, pp. 2752-2760, (2004).

(Continued)

Primary Examiner — Gerald Leffers, Jr.
Assistant Examiner — Magdalene Sgagias
(74) Attorney, Agent, or Firm — Winston & Strawn LLP

(57) ABSTRACT

The present invention relates in general to orthopedics and to a method for promoting repair of large bone defects, in particular non-union or delayed union fractures. Specifically the invention concerns the use of endothelial progenitor cell preparations for bone repair.

16 Claims, 10 Drawing Sheets

OTHER PUBLICATIONS

Isner, J. M. et al., "Angiogenesis and vasculogenesis as therapeutic strategies for postnatal neovascularization", Journal of Clinical Investigation, vol. 103, No. 9, pp. 1231-1236, (1999).

Kadiyala, S. et al., "Culture-expanded, bone marrow-derived mesenchymal stem cells can regenerate a critical-sized segmental bone defect", Tissue Engineering vol. 3, No. 2, pp. 173-188, (1997).

Kalka, C. et al., "Transplantation of ex vivo expanded endothelial progenitor cells for therapeutic neovascularization", Proc. Natl. Acad. Sci., vol. 97, No. 7, pp. 3422-3427, (2000).

Kaplan, R. N. et al., "VEGFR1-positive haematopoietic bone marrow progenitors initiate the pre-metastatic niche", Nature Publishing Group, vol. 438, No. 8, pp. 820-827, (2005).

LeGeros, PhD., R. Z., "Properties of osteoconductive biomaterials: calcium phosphates", Clinical Orthopaedics and Related Research, vol. 395, pp. 81-98, (2002).

Lewinson, D. et al., "Expression of vascular antigens by bone cells during bone regeneration in a membranous bone distraction system", Histochem. Cell Biol., vol. 116, pp. 381-388, (2001).

Lewinson, D. et al., "Revascularization during Bone Regeneration in Sheep Model of Maxillary Distraction", ASBMR 23rd Annual Meeting, J. Bone Miner Res. 16 (suppl 1), p. S329, (2001).

Lyden, D. et al., "Impaired recruitment of bone-marrow-derived endothelial and hematopoietic precursor cells blocks tumor angiogenesis and growth", Nature Medicine, vol. 7, No. 11, pp. 1194-1201, (2001).

Misty, A. S. et al., "Tissue engineering strategies for bone regeneration", Adv. Biochem. Engin. Biotechnol., vol. 94, pp. 1-22, (2005).

Murohara, T. et al., "Transplanted cord blood-derived endothelial precursor cells augment postnatal neovascularization", Journal of Clinical Investigation, vol. 105, No. 11, pp. 1527-1536, (2000).

Neumüller, J. et al., "Immunological and ultrastructural characterization of endothelial cell cultures differentiated from human cord blood derived endothelial progenitor cells", Histochem. Cell. Biol., vol. 126, pp. 649-664, (2006).

Pittenger, M. F. et al., "Multilineage potential of adult human mesenchymal stem cells", Science, vol. 284, pp. 143-147, (1999).

Rachmiel, A. et al., "Characterization of midface maxillary membranous bone formation during distraction osteogenesis", Plastic and Reconstructive Surgery, vol. 109, No. 5, pp. 1611-1620, (2002).

Ribatti, D., "The discovery of endothelial progenitor cells. An historical review", Leukemia Research, vol. 31, No. 4, pp. 439-444, (2007).

Richards, M. et al., "Marrow-derived progenitor cell injections enhance new bone formation during distraction", Journal of Orthopedic Research, vol. 17, No. 6, pp. 900-908, (1999).

Risau W. "Differentiation of endothelium", FASEB, vol. 9, pp. 926-933, (1995).

Risau, W. "Mechanisms of angiogenesis", Nature, vol. 386, pp. 671-674, (1997).

Risau, W. et al., "Vasculogenesis and angiogenesis in embryonic-stem-cell-derived embryoid bodies", Development, vol. 102, pp. 471-478, (1988).

Rozen, N. et al., "Role of Bone Regeneration and Turnover Modulators in Control of Fracture", Critical Reviews in Eukaryotic Gene Expression, vol. 13, No. 3, pp. 197-213, (2007).

Takahashi, T. et al., "Ischemia- and cytokine-induced mobilization of bone marrow-derived endothelial progenitor cells for neovascularization", Nature Medicine, vol. 5, No. 4, pp. 434-438, (1999).

Werner, N. et al., "Influence of Cardiovascular Risk Factors on Endothelial Progenitor Cells", Arteriosclerosis, Thrombosis, and Vascular Biology, vol. 26, pp. 257-266, (2006).

Yoshikawa, T. et al., "Immediate bone forming capability of prefabricated osteogenic hydroxyapatite", Journal of Biomedical Materials Research, vol. 32, pp. 481-492, (1996).

International Search Report PCT/IL07/00485 Dated Aug. 12, 2008.

U. Meyer et al., "Biological and Biophysical Principles in Extracorporal Bone Tissue Engineering Part I", Int. J. Oral Maxillofacial Surgery, vol. 33, pp. 325-332 (2000).

J. M. Polak et al., "Stem Cells and Tissue Engineering: Past Present, and Future", Ann. N.Y. Acad. Sci., vol. 1068, pp. 352-366 (2006).

Coleman, "Abstracts: 25th Annual Scientific Meeting of the Israel Society for Histochemistry and Cytochemistry held in the Rappaport Faculty of Medicine, Technion-Israel Institute of Technology, Haifa, Israel on May 29, 2006," Acta histochemica, 108:319-325 (2006).

Hisatome et al., "Neovascularization and bone regeneration by implantation of autologous bone marrow mononuclear cells," Biomaterials, 26:4550-4556 (2005).

* cited by examiner

Figure 2A
Figure 2B
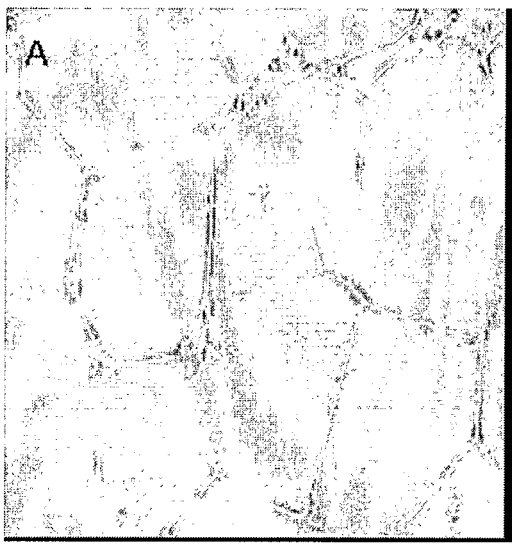
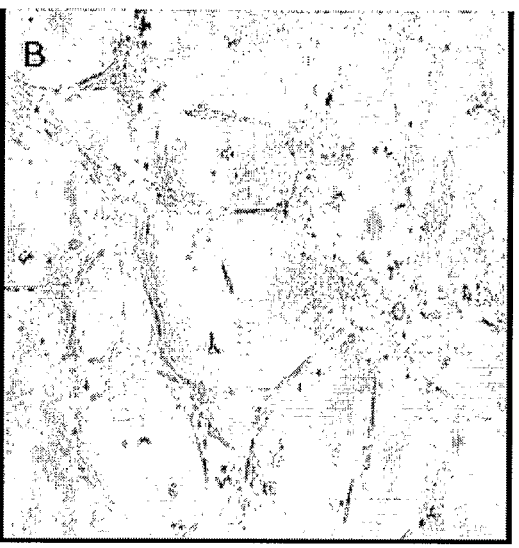

Figure 4A
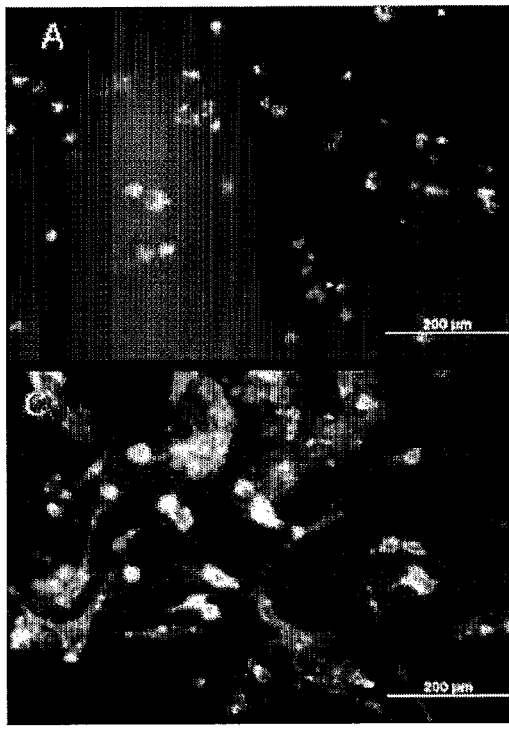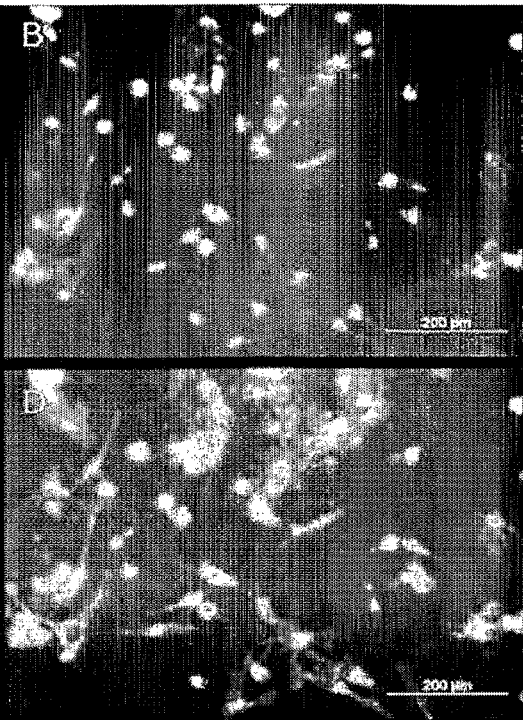
Figure 4B
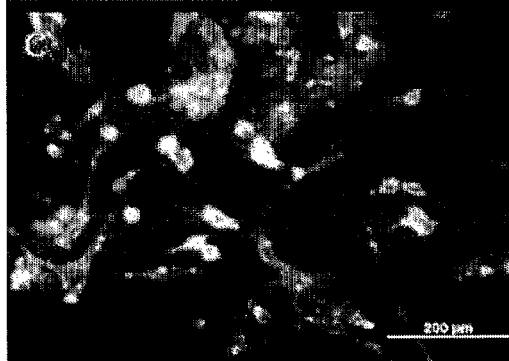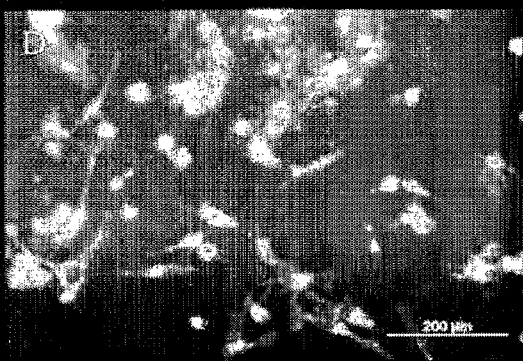
Figure 4C
Figure 4D

METHODS FOR BONE REGENERATION USING ENDOTHELIAL PROGENITOR CELL PREPARATIONS

This application is a 371 filing of International Patent Application PCT/IL2007/000485 filed Apr. 17, 2007, which claims the benefit of application No. 60/792,341 filed Apr. 17, 2006.

FIELD OF THE INVENTION

The present invention relates to a method for treating bone defects, in particular for promoting repair of large bone defects, including non-union and delayed union fractures. Specifically the invention concerns compositions comprising endothelial progenitor cells and methods of use thereof for bone repair.

BACKGROUND

Bone is a unique type of tissue composed of an inorganic mineral phase and cellular and extracellular matrix phases. Bone is a vital organ that undergoes modeling and remodeling wherein old bone is lost (resorption) and new bone is formed (replacement).

In children and young adults, bone remodeling results in the growth and increase in density of the skeleton. In adults, remodeling normally results in no net change in skeletal size since bone replacement matches bone resorption. Osteoporosis and related diseases ensue when bone resorption exceeds bone replacement. Bone restoration or replacement is a viable consideration in indications including osteopenia, osteoporosis, bone tumors, spinal fusion and fractures.

Each year, more than 6.3 million people in the U.S. experience bone fractures, of which almost 1 million require hospitalization. Natural healing of bone with mechanical fixation can, in most cases, adequately mend minor fractures over time. However, in approximately 10% of all fractures, the defect is too large for the body's natural healing response, and delayed unions or non-unions develop at the fracture site (Bancroft and Mikos, 2001; Rozen et al., 2007). In these cases, supplementary bone material may be required to fill in the defect and restore structure and function.

Current Therapies for Treatment of Severe Bone Defects

The standard treatment for healing severe bone defects is transplantation of autologous bone tissue (autografts) (reviewed in Mistry and Mikos, 2005). However, this process has several drawbacks including: limited body sites from which bone may be harvested without loss of function; autografts are less effective in irregularly shaped defects; and the procedure may be associated with complications such as infection, pain and nerve injury. Allografts derived from cadavers are another commonly used bone graft material. However, un-processed grafts carry a risk of disease transmission and immune rejection, while demineralized bone matrix is poor in bone growth inducing factors. Xenografts are also a poor option due to the danger of disease transmission or rejection.

Metal implants may be permanently placed in bone to fill a defect however corrosion, infection and poor implant-tissue interface create many problems.

Ceramics may also be used in the treatment of bone injuries. While offering excellent biocompatibility, they are often brittle and degrade too slowly thereby inhibiting natural bone re-growth.

Another potential treatment is distraction osteogenesis, which entails the lengthening of limbs across a defect through temporary external fixation devices.

As outlined above, the most advanced treatments are limited in effectiveness and are often associated with complications. Thus, there is a significant need for an alternative strategy for the treatment of severe bone loss or fracture.

Cell-Based Therapies

An emerging approach to damage repair is tissue engineering, which involves treatment with one or more of the following elements: cells, signaling molecules and scaffolds. Thus, by employing the body's natural healing response, a bone defect may be replaced by natural bone tissue in the absence of an exogenous permanent implant (Bancroft and Mikos, 2001; Rozen et al., 2007).

Cell-based strategies for bone tissue engineering involve, inter alia, the transplantation of osteogenic cells. Cell-based therapies may include fresh bone marrow, as well as mesenchymal stem cells (MSCs) expanded in culture, or differentiated osteoblasts. Autologous bone-marrow injected into patients' un-connected tibial fractures with fixation demonstrated efficacy equal to that of autografts (Connolly et al., 1991).

A key factor for the success of bone marrow in healing non-union fractures is the presence of MSCs. The limited quantity of MSCs in marrow has led to the development of methods to isolate progenitor cells from bone marrow and expand them in-vitro, prior to transplantation.

Richards et al., (1999) demonstrated the osteogenic capabilities of cultured MSCs in a collagen gel carrier injected into distraction gaps of rats. Kadiyala et al., (1997) loaded MSCs onto ceramic cylinders and implanted them into critical-sized defects in rat femora. In U.S. Pat. Nos. 6,541,024 and 6,863,900 to Kadiyala et al. regeneration and augmentation of bone repair following administration of MSCs was disclosed.

Isolated MSCs in culture can be selectively differentiated into osteoblasts with media supplements (Bruder et al., 1997; Pittenger et al., 1999). These osteogenic cells, when combined with a biomaterial carrier, can begin bone reconstruction immediately upon delivery to the injury site. For example, when rat marrow stromal cells cultured on porous hydroxyapatite scaffolds with osteogenic supplements were implanted subcutaneously in rats, rapid bone formation was observed (Yoshikawa et al., 1996).

U.S. Pat. No. 5,811,094 (Caplan et al.) provides a method for isolating, purifying, culturing and expanding human mesenchymal stem cells (MSCs) for the purpose of repairing connective tissue defects (including bone and cartilage repair). U.S. Pat. No. 6,355,239 (Bruder et al.) provides methods and preparations for promoting connective tissue growth, including bone, by transplanting allogeneic, mesenchymal stem cells.

U.S. Pat. No. 7,029,666 (Bruder et al.) demonstrates use of non-autologous MSCs for treatment and regeneration of connective tissue and enhancement of bone marrow engraftment.

U.S. Pat. No. 5,972,703 (Long et al.) discloses a process for preparing an enriched population of bone precursor cells (expressing osteocalcin or osteonectin) obtained from bone marrow for promoting bone fracture repair.

Endothelial Progenitor Cells

Endothelial progenitor cells (EPCs) have been identified in adult bone marrow as well as in peripheral blood and human umbilical cord blood, and have been shown to maintain their potency to proliferate and to differentiate into mature endothelial cells (Ashara et al., 1997; Murohara et al., 2000). Vasculogenesis, the development of new blood vessels during embryogenesis begins with the formation of blood islands comprising endothelial progenitor cells (EPCs) and hematopoietic stem cells (Risau, 1997; Risau, 1995; Risau et al., 1988; Flamme et al., 1992; Hatzopoulos et al., 1998; Doyle et al., 2006; Ribatti, 2007).

EPCs have been shown to participate in postnatal neovascularization (Takahashi et al., 1999; Isner and Asahara, 1999). Furthermore, EPCs were found to participate in angiogenesis, vascular repair and vasculoprotection (Humpert et al., 2005; Doyle et al., 2006).

Recent studies have shown that EPCs significantly participate in constructing endothelium of new vessels in situations of tissue regeneration such as burns, bypass coronary artery grafting, and acute myocardial infarction. In these instances, bone marrow-derived EPCs are recruited to the blood circulation and home to injured and regenerating tissues for their participation in the buildup of new blood vessels. For example, addition of a purified and ex-vivo expanded population of these cells to nude mice with hind limb ischemia improved blood flow recovery and reduced limb loss (Kalka et al., 2000). Moreover, growth factors and ischemic conditions augment the number of circulating EPC (Takahashi et al., 1999).

EPCs can be identified by tube formation in Matrigel™ (Bellik et al., 2005), acetylated low-density lipoprotein (Ac-LDL) incorporation or expression of characteristic cell markers including Tie-2, CD34+ and von Willebrand factor (vWf) (Neumuller et al., 2006).

Early studies in a distraction osteogenesis model in sheep described the appearance of cellular colonies of vascular nature (immunopositive for Tie-2 and factor VIII-related antigen), the origin of which was not clear (Rachmiel et al., 2002; Lewinson et al., 2001(a, b)).

Cetrulo et al., (2005) demonstrated that distraction osteogenesis in a rat mandible model results in the generation of an ischemic region, to which concomitantly injected human EPCs were shown to home.

U.S. Pat. No. 6,878,371 to Ueno et al. provides methods of forming new blood vessels in diseased or damaged tissue, specifically cardiac muscle comprising transplanting locally autologous bone marrow mononuclear cells.

Vascular injury was shown to promote an increase in circulating endothelial cells and EPCs (Hunting et al., 2005). In another study, bone marrow derived circulating EPCs were used to enhance angiogenesis following tissue ischemia (Werner et al. 2006).

U.S. Pat. No. 6,720,340 (Cooke et al.) discloses recruitment of bone marrow derived EPCs and hematopoietic stem cells to the site of deficiency or injury, by administration of nicotine or nicotine receptor agonists.

Nowhere in the background art is it taught or suggested that local transplantation of autologous endothelial progenitor cells augments bone regeneration and may therefore be used as a therapeutic strategy for critical-gap bone fracture repair. There remains an unmet need in the medical community for an effective treatment for non-union and delayed union fractures.

SUMMARY OF THE INVENTION

The present invention provides methods for treating bone defects comprising administering to the site of bone defect a composition comprising endothelial progenitor cells (EPCs). In contrast to other prevailing techniques that employ scaffolds into the area of bone defect, the current invention entails implantation of endothelial progenitor cells. Unlike MSCs, which are known to differentiate into bone cells, the current invention reveals the surprising finding that endothelial progenitor cells, which are known to promote vasculogenesis and angiogenesis, can also successfully promote bone regeneration. The present invention thus describes for the first time a therapeutic use of endothelial progenitor cells for repair of large bone defects.

In one of its aspects the present invention is directed to a method of repairing bone defects in a subject in need thereof by administering to the subject an effective amount of a cell preparation comprising endothelial progenitor cells (EPCs). EPCs can be identified by tube formation in Matrigel™, acetylated low-density lipoprotein (Ac-LDL) incorporation or expression of characteristic cell markers including Tie-2, CD34+ and von Willebrand factor (vWf).

In one embodiment the EPCs are injected systemically into the subject's blood circulation and home towards the bone defect area.

In a preferred embodiment the step of administering the cell preparation comprises applying said cell preparation locally to the site of bone defect. Local administration assures that the administered EPCs remain in the desired area, thereby allowing a direct and rapid effect of the cells on the injured tissue.

In one embodiment the administered EPCs are allogeneic, i.e. the cells originate from a member of the same species but not from the individual being treated.

In a preferred embodiment the administered EPCs are autologous, i.e. the cells are recovered from the individual being treated for the bone defect. The cells are isolated from the bone marrow or the peripheral blood and expanded ex-vivo to reach the desired cell number.

According to various embodiments the method of the invention is suitable for the repair of large bone defects, for example, non-union or delayed fractures, and critical sized bone defects caused by trauma, bone resection or radiotherapy.

In a certain embodiment of the present invention, the subject is a mammal. In a preferred embodiment the subject is human.

EPCs may be obtained from various sources including but not limited to bone marrow, peripheral blood and umbilical cord blood. Preferably, the EPCs are obtained by isolating mononuclear cells (MNC) from either the bone marrow, or from peripheral blood and expanding these cells in-vitro under conditions favorable for the expansion of endothelial cells. The cells may be derived from human CD34$^+$ mononuclear cells (EPC-enriched fraction).

In a particular embodiment a suspension of $10^6$-$10^{11}$ EPCs per ml in a pharmaceutically acceptable carrier is applied to the site of bone defect. In a preferred embodiment the EPCs are applied in a concentration of $10^7$-$10^{10}$ cells/ml. In a more preferred embodiment the EPCs are applied in a concentration of $10^8$-$10^9$ cells/ml.

The administration of EPCs may be performed at any time after the injury. According to some embodiments the EPCs are administered at least 10 days after the injury. According to another embodiment the EPCs are administered at least two weeks after the injury.

In a particular embodiment the EPCs may be administered in combination with other cell types, e.g. mesenchymal stem cells.

The EPCs may be administered alone or in combination with a conductive i.e. support material. Non-limiting examples of such conductive materials include paste (e.g. amorphous calcium phosphate paste, hydroxy apatite, calcium sulfate paste and demineralized bone), a natural or synthetic suitable scaffold (e.g. a fibrin matrix), a viscous milieu based on a biopolymer such as hyaluronic acid or a combination of these materials. Examples for suitable fibrin matrices may be found for example in U.S. Pat. No. 7,009,039, WO 2004/067704 and WO 2006/008748 assigned in part to the assignee of the present invention.

The EPCs may be administered in combination with an inductive material that would enhance their expansion in-vivo. Non limiting examples of inductive agents include growth factors. Examples for growth factors include: vascular endothelial growth factor (VEGF), fibroblast growth factor (FGF), epidermal growth factor (EGF), insulin-like growth factor 1 (IGF1), bone morphogenetic proteins (BMP), and transforming growth factor (TGF). In one embodiment EPCs are expanded ex-vivo with FGF, preferably with FGF2.

In another aspect, the present invention uses EPCs for the preparation of a pharmaceutical composition for repairing bone defects in a subject in need thereof. In yet another aspect, the present invention provides a pharmaceutical composition comprising EPCs and a pharmaceutically acceptable carrier for the treatment of bone defects.

These and further aspects of the current invention will be better understood in conjunction with the figures, detailed description, examples and claims that follow.

BRIEF DESCRIPTION OF THE FIGURES

FIG. 2 is a microphotograph of capillary-like structures formed by human umbilical vein endothelial cells (HUVEC) (A) and sheep EPC (B) plated in Matrigel™. The cells are shown at a magnification of ×10.

FIG. 4 is a microphotograph of sheep EPC (A) and HUVEC (B-D) stained with Dil-Ac LDL (A, B) and lectin (C). D shows double staining of HUVEC with Dil-Ac LDL and lectin. The cells are shown at a magnification of ×10.

DETAILED DESCRIPTION OF THE INVENTION

Figure 1A:
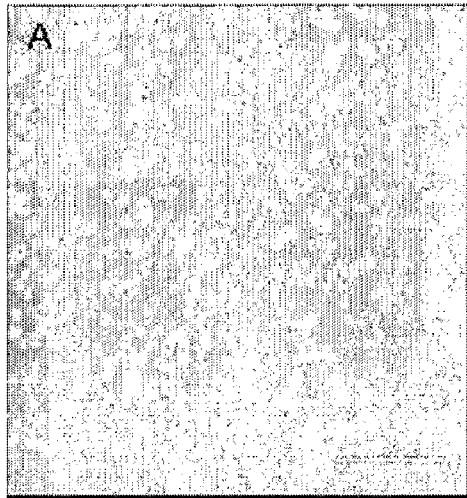
FIG. 1 is a microphotograph of human EPCs 3 days in culture (A, B) and after trypsinization and reseeding about 2 weeks afterwards (C, D). The cells are shown at a magnification of ×4 (A, C) and ×40 (B, D).
Figure 1B:
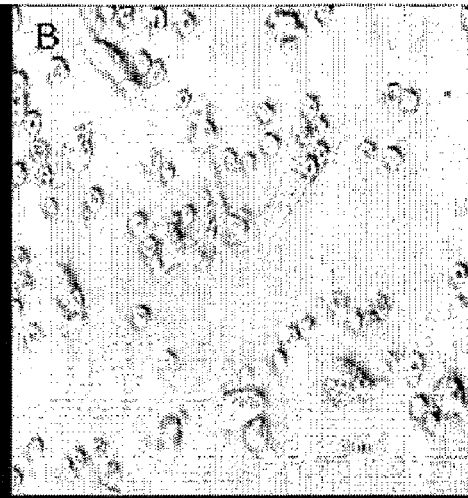
Figure 1C:
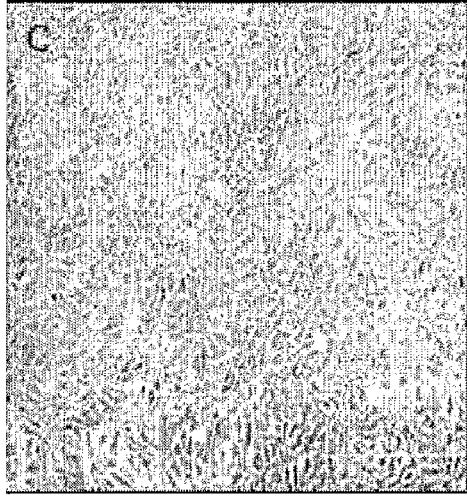
Figure 1D:
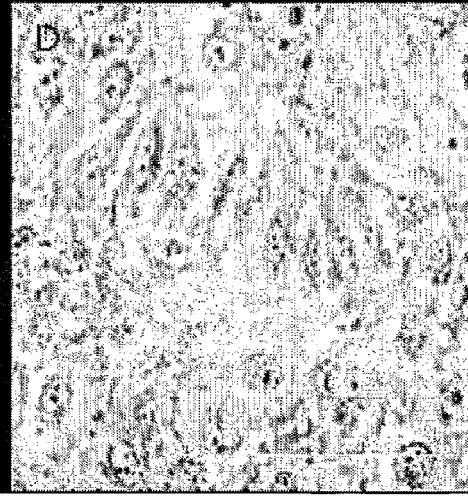

The present invention is directed to treatment of skeletal defects, in particular large bone gaps and non-union fragments, by implantation of endothelial progenitor cells (EPCs). This therapeutic method takes advantage of the natural healing process, enhanced by the addition of these growth (regeneration) promoting cells.

Several methods have been reported in the art to induce bone repair or enhance bone regeneration by implanting bone marrow or bone marrow derived mesenchymal stem cells (MSCs). MSCs are multipotent stem cells that can differentiate into a variety of cell types including osteoblasts, chondrocytes, myocytes, adipocytes, neuronal cells, and, as described lately, into pancreatic beta-islets cells. Since these cells can differentiate into bone cells, it is not surprising that they would enhance bone regeneration. Without wishing to be bound by any theory, the current invention discloses for the first time the finding that endothelial progenitor cells, which are known to promote vasculogenesis and angiogenesis, can also successfully promote bone regeneration.

The extraction of MSCs from peripheral blood is extremely difficult, and extraction from bone marrow yields only a limited quantity. In contrast, EPCs may be easily extracted from peripheral blood and expanded ex-vivo to obtain a sufficient quantity for implantation.

The advantages of this method include the following:
i) Regenerative capacity of EPCs, which are easily isolated and expanded ex-vivo.
ii) The surrounding healing tissue serves as a natural scaffold.
iii) Usage of autologous cells eliminates disease transmission and immunologic rejection and also minimizes the chances of infection.
iv) Implantation of endothelial progenitor cells directly to the damaged tissue reduces homing to other tissues thereby allowing efficient beneficial effect of the EPCs and also reducing the risk of promoting vascularization.
v) Obviates requirement for carrier, though the EPCs may be used in conjunction with methods employing scaffolds or carriers.

Bone is a vital organ that undergoes modeling and remodeling wherein old bone is lost (resorption) and new bone is formed (replacement). Although bone has an inherent capacity for repair and regeneration when damaged by disease or trauma, the renewed bone is often fragile and not weight bearing. Bone restoration or replacement is a viable consideration in indications including osteopenia, osteoporosis, bone tumors, spinal fusion, fractures and non-union fractures.

The process of bone formation is initiated by endochondral ossification and intramembranous ossification. Endochondral ossification is the fundamental mechanism for longitudinal bone formation whereby cartilage is replaced by bone. It requires the sequential formation and degradation of cartilaginous structures in the growth plates that serve as templates for the developing bones. During intramembranous ossification bone is formed directly in the connective tissues. Both processes require the infiltration of osteoblasts and subsequent matrix deposition. Bone formation may be enhanced either by recruiting osteoblasts, the bone forming cells, or by inhibiting recruitment or activity of osteoclasts, the bone resorbing cells. Osteoblasts and osteoclasts work together in a coordinated fashion to form and remodel bone tissue.

It is within the scope of the present invention to utilize compositions comprising EPCs, i.e. the compositions of the present invention, together with any such matrices or scaffolds as are known in the art.

Many materials have been suggested for bone repair, specifically materials that avoid the harvesting problems associated with autologous matter and the health risks associated with allogeneic material. Inorganic materials such as calcium phosphate have been utilized as bone and dental fillers (reviewed in LeGeros, Clin Orthop 395:81-98, 2002). Apatite, a particulate calcium phosphate, is particularly appealing by virtue of the fact that it is the naturally occurring mineral component in bone and teeth. Bone apatite exhibits low crystallinity due to the presence of magnesium and carbonate ($CO_3$) ions. Lack of crystallinity in apatites is associated with increased solubility in vivo. Hydroxyapatite, in contrast, exhibits high crystallinity and represents a small component of natural bone. Synthetic bone substitute materials comprising calcium phosphate or hydroxyapatite have been disclosed for use as bone grafts implants and cements. Highly crystalline form of hydroxyapatite can be produced by solution precipitation followed by sintering at high temperatures.

Various types of inorganic fillers or matrices that may be used in bone repair are well known. For example, U.S. Pat. No. 4,880,610 to Constantz teaches a method for producing an injectable calcium phosphate mineral bone-like material using highly concentrated phosphoric acid, a calcium source and a neutralizing source, to which various additives may be incorporated, including sugars or proteins such as collagen, fibrinogen or elastin. U.S. Pat. Nos. 5,650,176; 5,676,976 and 5,683,461 to Lee et al. teach the synthesis of reactive amorphous calcium phosphates (ACP) and their use for promoting bone growth.

It is further to be explicitly understood that the compositions and methods of the present may be used alone or in conjunction with other compositions and methods for bone repair as are known in the art. Thus, the EPCs are beneficial alone, but may be used together with other known cell types including but not limited to MSCs. Furthermore the EPCs may be administered in a composition comprising inert ingredients or within a composition comprising additional active ingredients such as known growth factors. The compositions comprising EPCs may be administered to the individual systemically or locally. According to currently preferred embodiments the administration is designed for local administration. For local administration it may be advantageous to add a supportive matrix or scaffold to assist in retaining the cells at the site of injury or fracture.

DEFINITIONS

For convenience and clarity certain terms employed in the specification, examples and claims are described herein.

As herein, the terms "bone defect" or "bone disorder" is meant an imbalance in the ratio of bone formation to bone resorption, such that, if unmodified, the subject will exhibit less bone than desirable, or the subject's bones will be less intact than desired. Bone deficit may also result from mutation, fracture, surgical intervention or from dental or periodontal disease.

Bones have a tremendous capacity for self-healing, and with proper treatment, most fractures will heal without complication. However, some fractured bones have difficulty healing. A "non-union fracture" occurs when a broken bone does not heal. When a bone is slow to heal, it is termed "delayed union fracture".

The term "critical bone gap" or "large bone gap" refer to bone gaps which are too large for spontaneous bone regeneration and require external interference.

Non limiting examples for bone defect are delayed or non-union fractures. Additional non-limiting examples are large bone defects caused by trauma, bone resection or radiotherapy.

Pharmacology

The term "therapeutic" refers to any pharmaceutical, drug or prophylactic agent which may be used in the treatment (including the prevention, diagnosis, alleviation, or cure) of a malady, affliction, disease or injury in a patient.

Pharmaceutical compositions suitable for use in context of the present invention include compositions wherein the active ingredients are contained in an amount effective to achieve the intended purpose. More specifically, a "therapeutically effective amount" relates an amount of a compound sufficient to promote bone regeneration. Determination of a therapeutically effective amount is well within the capability of those skilled in the art, especially in light of the detailed disclosure provided herein. The present invention contemplates pharmaceutical compositions, both for veterinary and for human medical use, which comprise as the active agent EPCs, as well as the use of EPCs in the manufacture of a medicament for the treatment of bone defects.

By the term "carrier" is meant any physiologically acceptable vehicle such as phosphate-buffered saline (PBS) or an analogous physiological solution including but not limited to biopolymers such as hyaluronic acid, viscous or non viscous vehicles, natural or synthetic vehicles, etc.

The dose of the pharmaceutical composition of the present invention may vary with the type of bone defect, the age of the patient, body weight, the route of administration, etc.; typically, it can be administered locally to the site of bone defect in a suspension of $10^6$-$10^{11}$ EPCs per ml of the pharmaceutically acceptable carrier.

Endothelial Progenitor Cells (EPCs)

The term "stem cell" refers to an undifferentiated cell that is capable of proliferation and further differentiation. Stem cells are capable of producing either new stem cells or cells called "progenitor cells" that differentiate to produce the specialized cells found in mammalian tissue and organs.

"Endothelial progenitor cells" (EPCs) refer to precursor cells produced in the bone marrow that are able of entering the bloodstream, reaching areas of blood vessel injury and participating in vascular repair. Studies have established that bone marrow-derived endothelial progenitor cells (EPCs) are present in the systemic circulation. They were also found to contribute to targeted tumor therapy. The current study demonstrates that these cells are also capable of participating in bone repair.

EPCs may be isolated from any one of bone marrow, peripheral blood or umbilical-cord blood. Isolation from peripheral blood, which is performed by density gradient centrifugation, provides sufficient quantities of EPCs to permit their harvest and administration following ex-vivo expansion. After culturing for 7 days, EPCs can be identified by demonstrating positive fluorescence staining for 1,1'-dioctadecyl-3,3,3',3'-tetramethylindocarbocyanine (DiI)-labeled acetylated low density lipoprotein (Ac-LDL) (Kalka et al., 2000). In addition, EPCs are characterized by homogenous staining for von Willebrand factor (vWF). EPCs also demonstrated spindle-like structures during maturation (Neumuller et al., 2006)

Cultured EPCs have a few advantages over freshly isolated CD34 antigen-positive (CD34+) EPCs. First of all, the number of EPCs obtained by ex-vivo expansion exceed the number of CD34+ cells that can be freshly isolated. Secondly, the purity and quality of EPCs in a cultured population are superior to that of freshly isolated CD34+ cells; as CD34+ was originally described as the prototypical antigen expressed by both HSCs and endothelial lineage cells, hematopoietic cells may contaminate freshly isolated CD34+ cells. Indeed, pilot studies demonstrated that the extent of neovascularization achieved after transplantation of freshly isolated CD34+ cells was inferior to culture-expanded EPCs. Thirdly, for therapeutic strategies designed to employ transplanted cells that constitutively express pro- or anti-angiogenic factors, gene transfer of EPCs is facilitated by the use of culture-committed vs. less-differentiated CD34+ EPCs (Kalka et al., 2000).

According to one aspect the present invention relates to a method of repairing bone defects in a subject in need thereof by administering to said subject an effective amount of a cell preparation comprising endothelial progenitor cells (EPC).

In a preferred embodiment the cell preparation is administered locally to the site of bone defect. Local administration ensures a direct and rapid effect of the cells on the injured tissue, and reduces homing to other tissues. In addition, local administration may have another advantage compared to injection of cells into the blood circulation, since bone marrow-derived EPCs along with hematopoietic progenitor cells were shown to contribute to the vascularization of specific primary tumors (Lyden et al., 2001; Kaplan et al., 2005). It may therefore be advisable to use local administration of the EPCs directly at the bone defect area.

The present invention is not limited by a method of preparing the implant. EPCs may be isolated from various sources including but not limited to bone marrow, peripheral blood and umbilical cord blood derived mononuclear cells (MNC). The cells may be freshly isolated from a mammalian subject (CD34+mononuclear cells, EPC-enriched fraction).

The term "autologous" as used herein, denotes that the cells are recovered from the individual being treated. The cells are isolated from the bone marrow or the peripheral blood and expanded in culture to reach the desired cell number.

The term "allogeneic" as used herein refers to being genetically different although belonging to or obtained from the same species.

The term "mammal" as used herein indicates human treatment as well as veterinary use.

In a preferred embodiment of the current invention, EPCs are obtained by isolating mononuclear cells (MNC) from either the bone marrow, or from peripheral blood of a mammal, expanding these cells in vitro under conditions favorable for the expansion of endothelial cells, and implanting the cells into the damaged tissue. In a preferred embodiment isolated EPCs are autologous to an individual in need of such treatment.

The term "conductive material" as used herein refers to a material which helps convey the EPC to the site of the bone defect. Use of a conductive material aims to enhance the therapeutic effect of the EPCs, by providing a milieu conducive to their survival or by aiding in retention of the cells at the site in need of repair.

The EPCs may be administered alone or in combination with a conductive support material. Non-limiting examples of such conductive materials include paste (e.g. amorphous calcium phosphate paste, hydroxy apatite, calcium sulfate paste and demineralized bone), a suitable scaffold (e.g. a fibrin matrix), a viscous milieu based on a biopolymer such as hyaluronic acid or a combination of these materials. Examples for suitable fibrin matrices may be found for example in U.S. Pat. No. 7,009,039; WO 2004/067704 and WO 2006/008748 assigned in part to the assignee of the present invention.

Amorphous calcium phosphate paste may be prepared according to the protocol exemplified hereinbelow, or by using any one of the other methods known in the art. Highly crystalline form of hydroxyapatite can be produced by solution precipitation followed by sintering at high temperatures.

The term "inductive material" as used herein refers to a substance which enhances the therapeutic (regenerative) effect of the EPCs. The inductive material may act directly to promote bone regeneration or it may act by promoting proliferation of the EPCs or both.

The EPCs may also be administered in combination with an inductive material such as a growth factor that would enhance their expansion in vivo. Non limiting examples of such growth factors are: vascular endothelial growth factor (VEGF), fibroblast growth factor (FGF) and their variants, including FGF2, FGF4, FGF9 and FGF18 which promote bone and cartilage healing, epidermal growth factor (EGF), insulin-like growth factor 1 (IGF1), bone morphogenetic proteins (BMP), and transforming growth factor (TGF).

FGFs comprise a large family of evolutionarily conserved polypeptides involved in a variety of biological processes including morphogenesis, angiogenesis, and tissue remodeling as well as in the pathogenesis of numerous diseases. The various members of this family stimulate the proliferation of a wide spectrum of cells, ranging from mesenchymal to epithelial and neuroectodermal origin in vitro and in vivo. FGFs are expressed in a strict temporal and spatial pattern during development and have important roles in patterning and limb formation. FGFs are powerful mitogens and are critical in the regulation of many biological processes including angiogenesis, vasculogenesis, wound healing, limb formation, tumorigenesis and cell survival.

FGFs and their analogs have been shown useful for treating indications including wounds (U.S. Pat. Nos. 4,950,483; 5,859,208 and 6,294,359), myocardial infarction (U.S. Pat. Nos. 4,296,100 and 4,378,347), skeletal disorders (U.S. Pat. Nos. 5,614,496 and 5,656,598) and remodeling cardiac tissue (U.S. Pat. No. 6,352,971).

WO 02/36732 and WO 03/094835 assigned in part to the assignee of the present invention disclose FGF variants, having at least one amino acid substitution in the beta 8-beta 9 loop, useful for the preparation of medicaments aimed at bone and cartilage formation and regeneration, wound healing, neovascularization and treating FGFR related skeletal and proliferative disorders. By way of non-limiting examples, the FGF2-N111X variants, including FGF2(3,5Q)-N111X, are more potent mitogens than the native FGF2.

Growth factors may be administered at a wide range of concentrations, depending on the type of bone defect, the age of the patient, body weight, the route of administration, etc.

"Mesenchymal stem cells" or MSCs as referred to herein are multipotent stem cells which can differentiate into a variety of cell types. EPCs may also be administered in combination with other cell types, e.g. mesenchymal stem cells, which would enhance their regenerative effect.

The term "implantation" as used herein refers to the insertion of the composition of the invention into damaged tissue, whereby the implant serves to promote the regeneration of the tissue that has been damaged or removed.

EPCs can be injected systemically into the subject's blood circulation or implanted directly onto the area of bone defect. In a preferred embodiment the cell preparation is administered locally to the area of bone defect. Local administration ensures that most of the implanted EPCs reach the defected tissue and reduces homing to other tissues, thereby allowing a direct and rapid effect of the cells on the injured tissue. A further advantage of direct implantation over injection of cells into the blood circulation, is reducing the risk of contributing to the vascularization of specific primary tumors. Local administration may be performed via several procedures, including but not limited to open surgery and direct injection to the site of bone defect guided by either x-ray or an endoscope which is inserted through a small incision in the skin.

Another aspect of the invention is a pharmaceutical composition comprising EPC for repairing bone defects.

The following examples are intended to be merely illustrative in nature and to be construed in a non-limitative fashion.

Examples

Example 1

Ex-Vivo Expansion and Characterization of EPC

Isolation and Culture of EPC from Bone Marrow Derived and Peripheral Blood Derived Mononuclear Cells (MNC)

EPC were prepared from sheep mononuclear cells (MNC). Mononuclear cells (MNC) were separated from the bone-marrow of a removed tibia segment (3.2 cm) or from samples of 10 to 40 ml of peripheral venous blood taken from the jugular vein, using Uni-Sep$_{MAXI}$® U-16 Ficoll™ (Novamed, Jerusalem, Israel) by density gradient centrifugation at 400×g for 30 min at room temperature (RT). The MNC fraction was collected, washed twice, by centrifugation at 200×g for 15 min, with 45 ml Dulbecco's phosphate-buffered saline (DPBS, without calcium and magnesium; Biological Industries Ltd., Beit Haemek, Israel) containing 3% fetal calf serum (FCS; Biological Industries Ltd., Beit Haemek, Israel), and plated on fibronectin-coated six-well plates (Sigma Chemical Co., St. Louis, Mo.). Cells were cultured in endothelial basal medium-2 (EBM-2; Clonetics, Walkersville, Md., USA), supplemented with EGM-2MV SingleQuot® containing 5% fetal bovine serum, vascular endothelial growth factor (VEGF), fibroblast growth factor-2, epidermal growth factor, insulin-like growth factor-1 and ascorbic acid. Cells were grown at 37° C. with humidified 95% air/5% $CO_2$. The initially seeded cells were round. After 3-5 days, attached cells appeared elongated and spindle shaped (FIG. 1).

After 6 days of culture, non-adherent cells were discarded by gentle washing with PBS, and fresh medium was applied. The attached cells were continually cultured with complete endothelial growth medium-2 (EGM-2 medium). Cells were fed 3 times per week and split when confluent by brief trypsinization using 0.5% trypsine/0.2% EDTA (Biological Industries Ltd., Beit Haemek, Israel) and dispersed. The re-plated cells rapidly replicated from several cells to colonies and formed a monolayer with full confluence (FIG. 1). These cells were expanded and underwent serial passages while maintaining a homogenous appearance, and were characterized thereafter.

Characterization of Mononuclear Cell Derived EPC

The incubated cells were identified as EPC using the following criteria: tube formation in Matrigel™, Ac-LDL incorporation and expression of von Willebrand factor (vWf).

Tube formation in Matrigel™: For demonstration of capillary tube formation, 250 µl of growth factor-reduced Matrigel™ (BD Biosciences Discovery Labware, Bedford, Mass.) was added per well of a 24-well plate and allowed to polymerize at 37° C. for at least 30 min. Adherent cells (suspected to be EPC) or human umbilical vein endothelial cells (HUVEC, which serve as an endothelial cell positive control) were trypsinized and $5×10^4$ cells were re-suspended in 300 µl EGM2-MV medium and seeded onto Matrigel™ (Ingram et al. 2004). The cells were incubated at 37° C. with humidified 95% air/5% $CO_2$ for 5-24 h. The tube networks were observed with an Olympus inverted microscope (Olympus, CKX41-RFA). When placed in Matrigel™-based media the cells rapidly formed capillary-like structures similar to those formed by HUVEC in Matrigel™ (FIG. 2).

Acetylated LDL (Ac-LDL) incorporation: To confirm the EPC phenotype, adherent cells were incubated with 10 mg/ml Ac-LDL coupled with fluorescent 1,1'-dioctadecyl-3,3,3',3'-tetra-methyl-indocarbocyanide perchlorate (Dil-Ac-LDL) (Molecular Probes Inc., Eugene, Oreg., USA) for 3-24 hours (Ingram et al. 2004). Cells were visualized with an Olympus CXK41 inverted fluorescent microscope. These cells demonstrated the ability to rapidly incorporate Ac-LDL (FIG. 4) indicating EPC characteristics. Also, Ac-LDL staining of sheep EPC was similar to the staining of HUVEC.

Figures 3A, 3B:
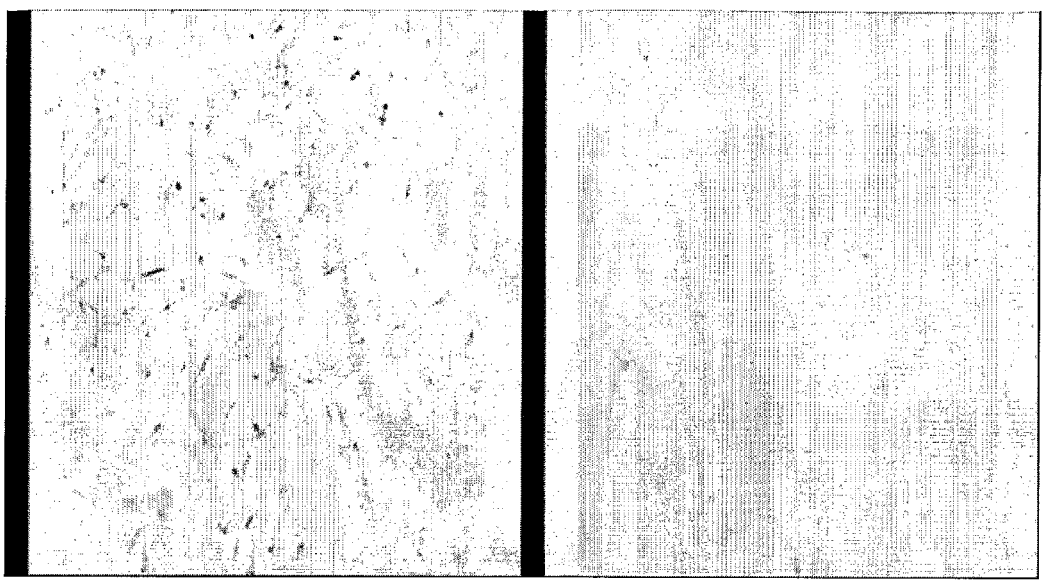
FIG. 3 is a microphotograph of sheep EPC positively stained for cytoplasmic Von Willebrand factor (vWf) (left panel). The right panel shows cells stained without the primary anti-vWf antibody (as negative control). The cells are shown at a magnification of ×10.

Von Willebrand factor (vWf): On day 7 of culture, adherent cells were trypsinized, seeded and grown on chamber-slides for 2-3 days. Slides were subjected to immunocytochemistry to detect the expression of vWf. In brief, following fixation with 4% paraformaldehyde for 10 min at 4° C. and endogenous peroxidase inactivation immunostaining was performed. After 3 washes with PBS, slides were incubated with rabbit anti human vWf diluted 1:50 (DAKO, Glostrup, Denmark) for 1 hour, RT. Negative control slides were incubated without the antibody. After 3 washes with PBS, slides were incubated for 10 min with HRP polymer conjugate (SuperPicTure™ Polymer Detection Kit-Zymed Laboratories, San Francisco, Calif., USA). To visualize the final immunoreaction products, AEC (RED) substrate (SuperPicTure™ Polymer Detection Kit-Zymed Laboratories, San Francisco, Calif., USA) was incubated with the slides for 5 min. Immunohistochemical staining of these cells demonstrated the presence of vWf (FIG. 3)

Example 2

A Critical Gap Model in Sheep Tibiae

Figure 5A:
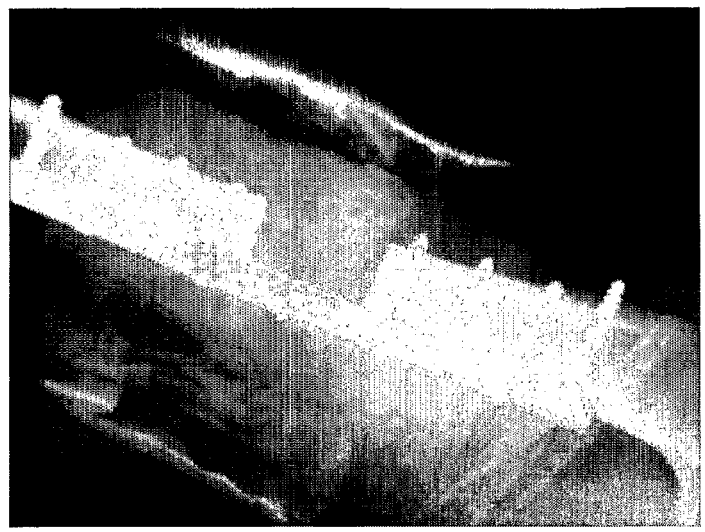
FIG. 5 is an X-ray radiograph of sheep tibia with a critical gap of 3.2 cm at the day of bone removal (A). (B) is an X-ray radiograph of the critical gap taken two weeks after bone removal prior to EPC or paste implantation.
Figure 5B:
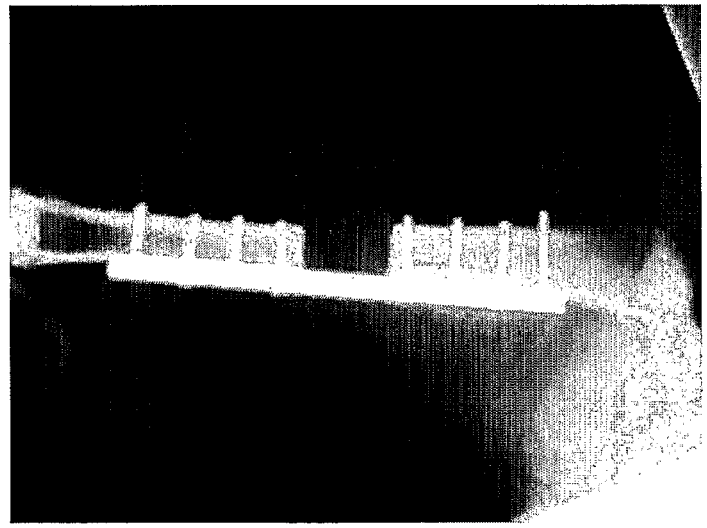
Figure 6A:
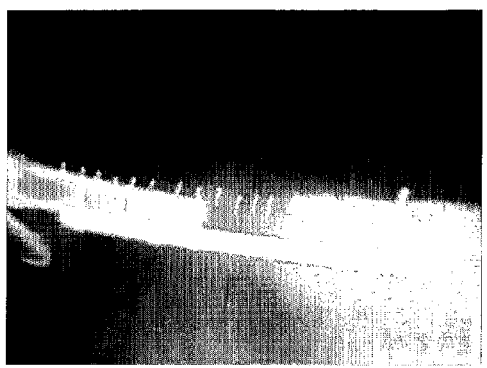
FIG. 6 is an X-ray radiograph of the critical gap taken 2 weeks post treatment with EPC and/or paste versus control. (A) control; (B) treated with EPC; (C) treated with paste; (D) treated with both paste and EPC.
Figure 6B:
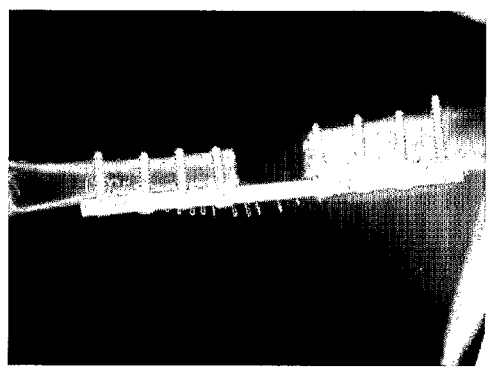
Figure 6C:
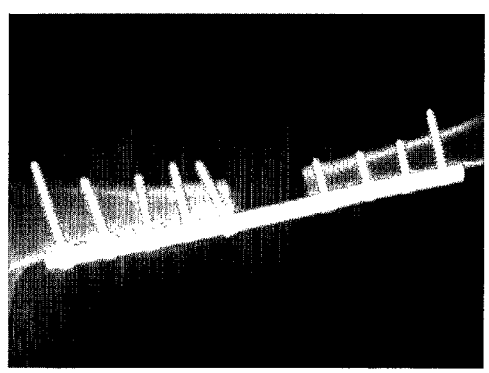
Figure 6D:
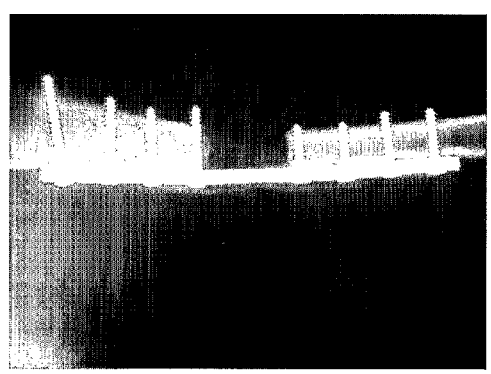
Figure 7A:
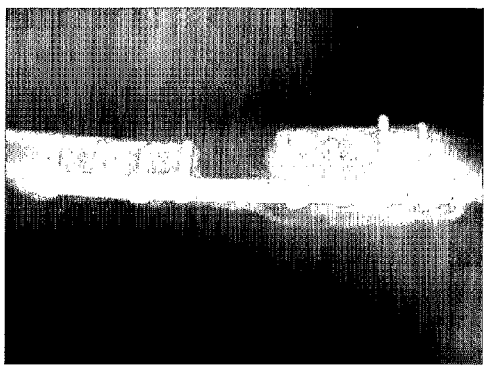
FIG. 7 is an X-ray radiograph of the critical gap taken 4 weeks post treatment with EPC and/or paste versus control. (A) control; (B) treated with EPC; (C) treated with paste; (D) treated with both paste and EPC.
Figure 7B:
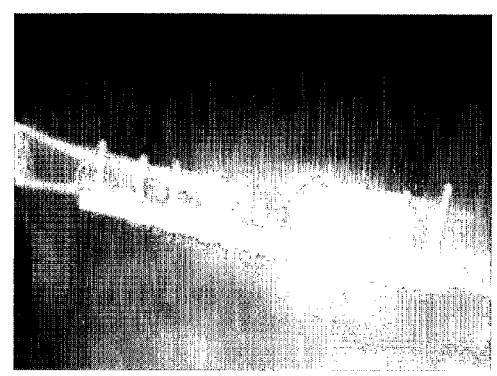
Figure 7C:
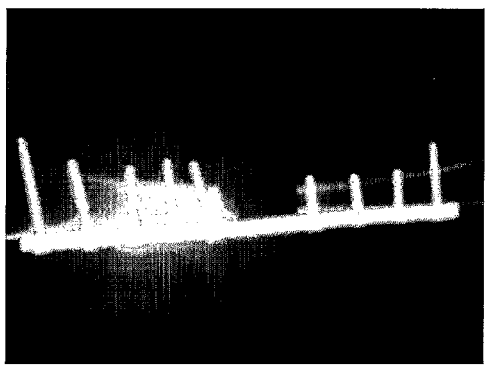
Figure 7D:
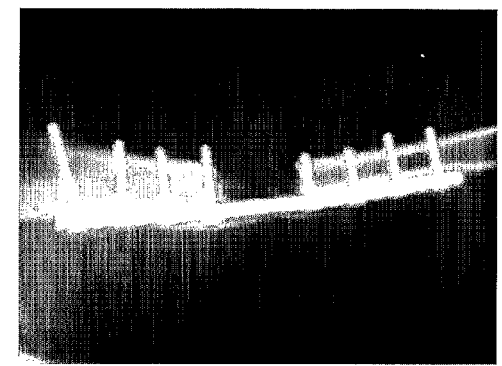
Figure 8A:
FIG. 8 is an X-ray radiograph of the critical gap taken 8 weeks post treatment with EPC and/or paste versus control. (A) control; (B) treated with EPC; (C) treated with paste; (D) treated with both paste and EPC.
Figure 8B:
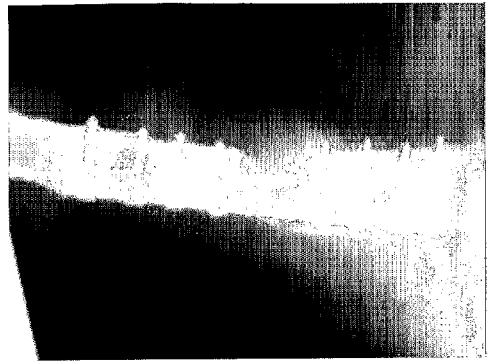
Figure 8C:
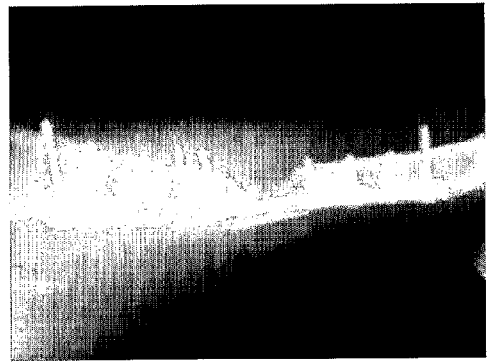
Figure 8D:
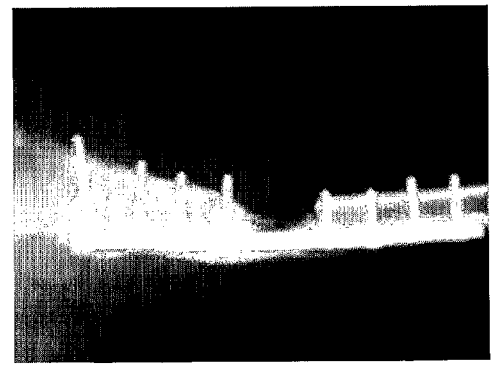
Figure 9A:
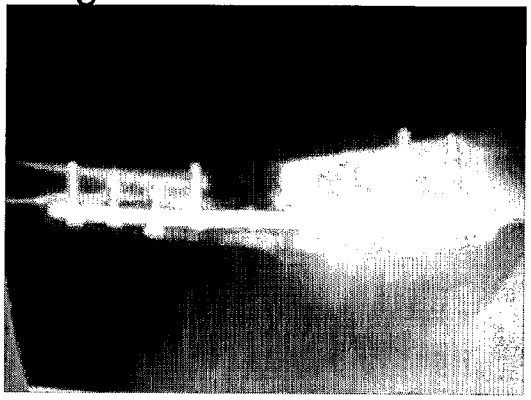
FIG. 9 is an X-ray radiograph of the critical gap taken 12 weeks post treatment with EPC and/or paste versus control. (A) control; (B) treated with EPC; (C) treated with paste; (D) treated with both paste and EPC.
Figure 9B:
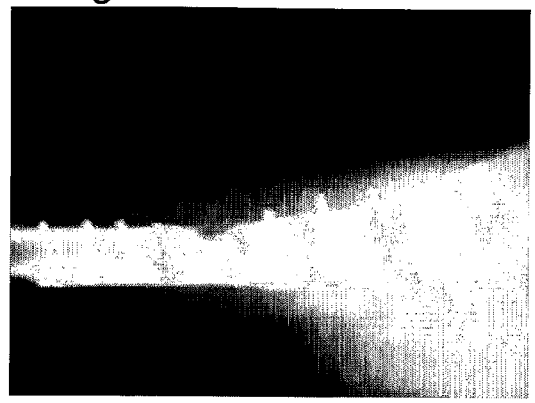
Figure 9C:
Figure 9D:
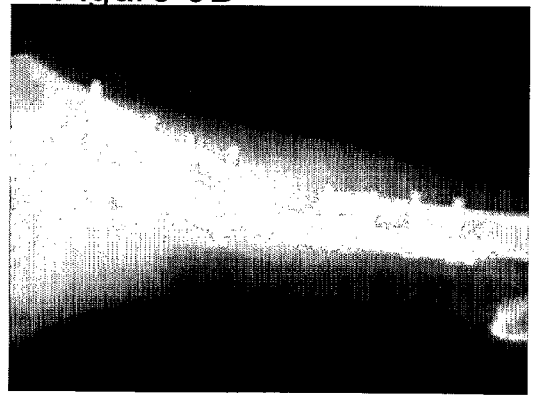
Figure 10A:
FIG. 10 is a Micro Computed Tomography (µCT) 3D visualization of the critical gap 12 weeks post implantation versus control. (A) control; (B) treated with EPC; (C) treated with paste; (D) treated with both paste and EPC.
Figure 10B:
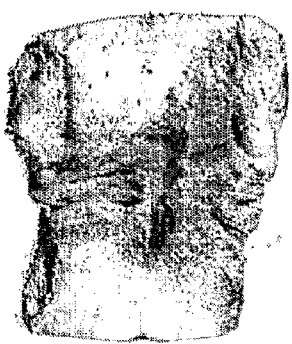
Figure 10C:
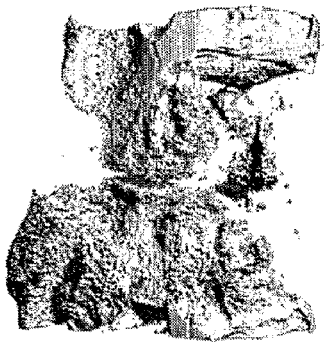
Figure 10D:
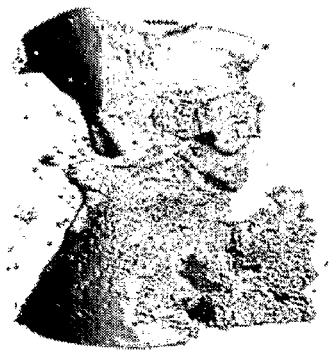

A critical bone gap model was generated by removing a 3.2 cm bone segment from sheep tibia (FIG. 5). Anesthesia was performed in 13 sheep (aged about 2 years, 40-70 Kilograms) by 0.4 xylasin and 600 mg ketamin, induced by 200 mg propapol and maintained by an intubation of 2% isofloran and oxygen ventilation. One gm cephazoline was given during surgery and then amoxilin 6 ml twice a day for the next 10 days. A longitudinal incision was performed along the skin of the anterior aspect of the right lower leg. The periosteum was similarly cut and elevated. Following the adjustment of a metal plate by 8 screws to the posterior aspect of the tibia, a segment of 3.2 cm was removed from the mid-diaphysis. This segment was preserved on ice for future isolation and culture of autologous EPC (as described above). Periosteum, fascia and skin were replaced and closed by sutures and pins and sprayed with antibiotics. A plaster cast was placed over the tibia and was removed one week later. All surgical procedures were approved by the Institutional Animals Health and Care Committee.

Example 3

Implantation of EPC or Paste into a Critical Bone Gap

Preparation of Amorphous Calcium Phosphate Paste 1.3 gr of Hydroxyapatite (ProChon Biotech) was dissolved in 10 ml of phosphate buffered saline (PBS). Following filtration, 2.5 gr of Hyaluronic acid (MW $3\times10^6$ in 1% concentration, ProChon Biotech) were added.

Amorphous Calcium Phosphate Paste Containing FGF 1.3 gr of Hydroxyapatite (ProChon Biotech) was dissolved in 10 ml of phosphate buffered saline (PBS). 25 μgr/ml FGF2 (3,5Q)-N111G (an FGF2 variant disclosed in WO 03/094835 assigned in part to the assignee of the present invention) was precipitated on the Hydroxyapatite for 1 hr at 37° C. Following filtration, 2.5 gr of Hyaluronic acid (MW $3\times10^6$ in 1% concentration, ProChon Biotech) were added.

Two weeks after the removal of the bone segment, the sheep underwent a second operation using the same procedures. A nicely enveloped healing tissue was observed filling the whole segmental gap. A longitudinal wedged-shaped incision was made within the gap. Each sheep received a different treatment:

In 3 sheep the gap was filled with 200 microliter of phosphate buffered saline (PBS) and covered by the wedged-shaped excised tissue. These sheep served as segmental defect controls.

In 5 sheep the gap was filled by a suspension of about $2\times10^7$ EPC in 200 microliter of PBS ($10^8$ EPCs per ml) and covered by the wedged-shaped excised tissue In one sheep the gap was filled by a suspension of about $2\times10^7$ EPC in 200 microliter of PBS ($10^8$ EPCs per ml) that was layered upon a layer of an amorphous calcium phosphate paste and then covered by another layer of the paste.

In one sheep the gap was filled only by amorphous calcium phosphate paste and in 3 additional sheep the gap was filled by amorphous calcium phosphate paste containing 25 μgr/ml FGF2(3,5Q)-N111G (an FGF2 variant disclosed in WO 03/094835 assigned in part to the assignee of the present invention).

Example 4

Radiological Follow-Up

In each sheep, the right lower leg was X-rayed every 2 weeks until the animal was sacrificed after 3 months of healing. Upon sacrifice, the healed gap with the limiting bone edges were excised and immersed in neutral-buffered formalin for 4 days which was then replaced by 70% alcohol. The specimens were then scanned by μCT (Micro Computed Tomography). This method is used for taking qualitative and quantitative total bone volume, mineralized bone volume and bone mineral density measurements.

Compared to control gaps, bone regeneration bridging the whole length of the defect was observed in all five experimental sheep. FIGS. 6-9 demonstrate time course of bone regeneration in one representative sheep from each treatment group. In sheep where the gap was implanted with EPCs, a weak cloudy opaqueness along the gap was observed already 2 weeks following the implantation of the cells (FIG. 6). It gradually increased in volume and density until complete bridging was observed by the time of sacrifice, 12 weeks after the implantation. In sheep where the gap was filled either with paste, paste containing FGF or paste plus cells, the regeneration process Was somewhat slower. However, in these sheep a marked bone formation bridged the gap by 12 weeks of healing (FIGS. 7-9). The control gap showed no bridging, except for a small radio-opaque focus after 4 weeks in the middle of the gap or minor mineralization along the plate, that did not develop any further. Table 1 shows quantitative evaluation of x-ray radiographs for gap mineralization at sacrifice for each sheep, where prox denotes an area 5 mm proximal to the gap center, and dist denotes an area 5 mm distal to the gap center. Bone formation was scored on a scale from 0 to ++++, where 0 denotes negative results and ++++ denotes complete bridging.

TABLE 1

Quantitative evaluation of gap mineralization at sacrifice

|  | center | prox | dist |
| --- | --- | --- | --- |
| Control | + | 0 | 0 |
|  | + | + | + |
|  | 0 | 0 | 0 |
| EPC | +++ | ++++ | ++++ |
|  | ++++ | ++++ | ++++ |
|  | ++++ | ++++ | ++++ |
|  | ++++ | ++++ | ++++ |
|  | ++++ | ++++ | ++++ |
| Paste | + | ++ | ++ |
| Paste + FGF | +++ | +++ | +++ |
|  | ++ | ++ | + |
|  | +++ | +++ | + |
| Paste + EPC | 0 | + | + |

μCT 3D visualization (presented in FIG. 10) confirmed the x-ray results demonstrating a very dense trabecular bone formation in gaps filled with EPC, minor mineralization in control sheep and partial bridging/mineralization in gaps filled with either paste+FGF or paste+EPC.

Representative quantitative analyses of bone formation (μCT imaging system, Scanco Medical, Basserdorf, Switzerland, at a resolution of 36 micrometer), is presented in Table 2.

TABLE 2

μCT quantitative analysis for representative sheep

| Sheep Identification | Total Tissue Volume (mm$^3$) | Bone Volume (mm$^3$) | Material Density (mg HA/cm$^3$) |
| --- | --- | --- | --- |
| Control | 2240.2 | 1008.3 | 329.75 |
| EPC | 11002.8 | 7854.3 | 705.16 |
| Paste | 4444.6 | 2789.0 | 615.59 |
| Paste + EPC | 2729.2 | 2034.6 | 440.58 |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

Asahara T, Murohara T, Sullivan A, Silver M, van der Zee R, Li T, Witzenbichler B, Schatteman G, Isner J M. Isolation of putative progenitor endothelial cells for angiogenesis. Science 275:964 (1997)

Bancroft, G N and Mikos, A G Bone tissue engineering by cell transplantation. In: Ikada Y, Oshima N (eds) Tissue engineering for therapeutic use 5. Elsevier, New York, p 151 (2001).

Bellik L, Ledda F, Parenti A. Morphological and phenotypical characterization of human endothelial progenitor cells in an early stage of differentiation. FEBS Lett. 579(12):2731-6 (2005).

Bruder S P, Jaiswal N, Haynesworth S E. Growth kinetics, self-renewal, and the osteogenic potential of purified human mesenchymal stem cells during extensive subcultivation and following cryopreservation. J Cell Biochem. 64(2):278-94 (1997).

Cetrulo C L Jr, Knox K R, Brown D J, Ashinoff R L, Dobryansky M, Ceradini D J, Capla J M, Chang E I, Bhatt K A, McCarthy J G, Gurtner G C. Stem cells and distraction osteogenesis: endothelial progenitor cells home to the ischemic generate in activation and consolidation. Plast Reconstr Surg. 116(4):1053-64; discussion 1065-7 (2005).

Connolly J F, Guse R, Tiedeman J, Delme R. Autologous marrow injection as a substitute for operative grafting of tibial non-unions. Clin Orthop Relat Res. (266):259-70 (1991)

Doyle B, Metharom P, Caplice N M. Endothelial progenitor cells. Endothelium. 13(6):403-10. (2006)

Flamme I, Risau W. Induction of vasculogenesis and hematopoiesis in vitro. Development. 116(2):435-9 (1992)

Hatzopoulos A K, Folkman J, Vasile E, Eiselen G K, Rosenberg R D. Isolation and characterization of endothelial progenitor cells from mouse embryos. Development. 125(8): 1457-68. (1998)

Ingram D A, Mead L E, Tanaka H, Meade V, Fenoglio A, Mortell K, Pollok K, Ferkowicz M J, Gilley D, Yoder M C. Identification of a novel hierarchy of endothelial progenitor cells using human peripheral and umbilical cord blood. Blood. 104(9):2752-60. (2004)

Isner J M and Asahara T Angiogenesis and vasculogenesis as therapeutic strategies for postnatal neovascularization. J Clin Invest. 103(9): 1231-6. Review. (1999)

Kadiyala S, Jaiswal N, Bruder S P Tissue Engineering Strategies for Bone Regeneration Tissue Eng 3:173.42. (1997)

Kalka C, Masuda H, Takahashi T, Kalka-Moll W M, Silver M, Kearney M, Li T, Isner J M, Asahara T. Transplantation of ex vivo expanded endothelial progenitor cells for therapeutic neovascularization. Proc Natl Acad Sci USA. 97(7):3422-7. (2000)

Kaplan R N, Riba R D, Zacharoulis S, Bramley A H, Vincent L, Costa C, MacDonald D D, Jin D K, Shido K, Kerns S A, Zhu Z, Hicklin D, Wu Y, Port J L, Altorlki N, Port E R, Ruggero D, Shmelkov S V, Jensen K K, Rafii S, Lyden D. VEGFR1-positive haematopoietic bone marrow progenitors initiate the pre-metastatic niche. Nature. 438(7069):820-7. (2005)

LeGeros R Z. Properties of osteoconductive biomaterials: calcium phosphates. Clin Orthop Relat Res. 395:81-98. (2002)

Lewinson D, Maor G, Rozen N, Rabinovich I, Stahl S, Rachmiel A. Expression of vascular antigens by bone cells during bone regeneration in a membranous bone distraction system. Histochem Cell Biol. 116(5):381-8.(2001a)

Lewinson D, Rachmiel A, Shenzer P. Revascularization during Bone Regeneration in Sheep Model of Maxillary Distraction. J. Bone Miner Res. 16 (suppl 1): S329 (2001b)

Lyden D, Hattori K, Dias S, Costa C, Blaikie P, Butros L, Chadburn A, Heissig B, Marks W, Witte L, Wu Y, Hicklin D, Zhu Z, Hackett N R, Crystal R G, Moore M A, Hajjar K A, Manova K, Benezra R, Rafii S. Impaired recruitment of bone-marrow-derived endothelial and hematopoietic precursor cells blocks tumor angiogenesis and growth. Nat Med. 7(11): 1194-201. (2001)

Mistry A S and Mikos A G Tissue engineering strategies for bone regeneration. Adv Biochem Eng Biotechnol. 94:1-22. Review. (2005)

Murohara T, Ikeda H, Duan J, Shintani S, Sasaki K, Eguchi H, Onitsuka I, Matsui K, Imaizumi T. Transplanted cord blood-derived endothelial precursor cells augment postnatal neovascularization. J Clin Invest. 105(11):1527-36. (2000)

Neumuller J, Neumuller-Guber S E, Lipovac M, Mosgoeller W, Vetterlein M, Pavelka M, Huber J. Immunological and ultrastructural characterization of endothelial cell cultures differentiated from human cord blood derived endothelial progenitor cells. Histochem Cell Biol. 126(6):649-64. (2006)

Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. Science 284(5411):143-7. (1999)

Rachmiel A, Rozen N, Peled M, Lewinson D. Characterization of midface maxillary membranous bone formation during distraction osteogenesis. Plast. Reconstr. Surg. 109 (5):1611-20. (2002)

Ribatti D. The discovery of endothelial progenitor cells An historical review. Leuk Res. (4):439-44. (2007)

Richards M, Huibregtse B A, Caplan A I, Goulet J A, Goldstein S A. Marrow-derived progenitor cell injections enhance new bone formation during distraction. J Orthop Res 17(6):900-8. (1999)

Risau W, Sariola H, Zerwes H G, Sasse J, Ekblom P, Kemler R, Doetschman T. Vasculogenesis and angiogenesis in embryonic-stem-cell-derived embryoid bodies. Development 102(3):471-8. (1988)

Risau W. Differentiation of endothelium. FASEB J. 9(10): 926-33. Review. (1995)

Risau W. Mechanisms of angiogenesis. Nature. 386(6626): 671-4. Review. (1997)

Rozen N, Lewinson D, Bick T, Meretyk S, Soudry M, Role of Bone Regeneration and Turnover Modulators in Control of Fracture, Critical Reviews in Eukaryotic Gene Expression Vol. 13, Issue 3 (2007)

Takahashi T, Kalka C, Masuda H, Chen D, Silver M, Kearney M, Magner M, Isner J M, Asahara T. Ischemia- and cytokine-induced mobilization of bone marrow-derived endothelial progenitor cells for neovascularization. Nat Med. 5(4):434-8. (1999)

Yoshikawa T, Ohgushi H, Tamai S Immediate bone forming capability of prefabricated osteogenic hydroxyapatite. J Biomed Mater Res. 32(3):481-92. (1996)

The invention claimed is:

1. A method of repairing a bone defect in a subject in need thereof which comprises administering to the subject a therapeutically effective amount of a cell preparation comprising endothelial progenitor cells and a pharmaceutically acceptable carrier, wherein the endothelial progenitor cells are administered in a range of concentrations of $10^7$-$10^{11}$ cells per ml of the pharmaceutically acceptable carrier.

2. The method according to claim 1, wherein the cell preparation is administered by applying the cell preparation locally to an area of bone defect.

3. The method according to claim 1, wherein the endothelial progenitor cells are allogeneic or are recovered from the individual being treated.

4. The method according to claim 1, wherein the bone defect is a delayed or non-union fracture or a bone defect caused by trauma, bone resection or radiotherapy, and the subject is a mammal or human.

5. The method according to claim 1, wherein the endothelial progenitor cells are obtained from bone marrow-derived mononuclear cells or peripheral blood-derived mononuclear cells or are derived from human CD34+ mononuclear cells.

6. The method according to claim 1, wherein the range of concentrations of endothelial progenitor cells is $10^7$-$10^{10}$ cells per ml of the pharmaceutically acceptable carrier.

7. The method according to claim 1, wherein the bone defect is caused by an injury and the cell preparation is administered at least 10 days after the injury or at least two weeks after the injury.

8. The method according to claim 1, wherein the cell preparation further comprises mesenchymal stem cells.

9. The method according to claim 2, which further comprises administering to the subject a conductive material of a paste, a scaffold or a viscous biopolymer.

10. The method according to claim 9, wherein a conductive paste is administered, wherein the paste comprises an amorphous calcium phosphate paste, hydroxy apatite, calcium sulfate paste or demineralized bone.

11. The method according to claim 1, which further comprises administering to the subject an inductive material of a growth factor selected from the group consisting of vascular endothelial growth factor, fibroblast growth factor, epidermal growth factor, insulin-like growth factor 1, bone morphogenetic proteins, and transforming growth factor.

12. The method according to claim 5, wherein the bone marrow-derived mononuclear cells incorporate Ac-LDL following culture or express Von Willebrand factor (vWf) following culture.

13. The method according to claim 5, wherein the peripheral blood-derived mononuclear cells incorporate Ac-LDL, express Von Willebrand factor (vWf), or form tubes following culture.

14. The method according to claim 9, wherein a viscous biopolymer is administered, wherein the viscous biopolymer comprises hyaluronic acid.

15. A method of repairing a bone defect in a subject in need thereof which comprises administering to the subject a therapeutically effective amount of a cell preparation comprising endothelial progenitor cells, a pharmaceutically acceptable carrier and a viscous biopolymer, wherein the endothelial progenitor cells are allogeneic or are recovered from the individual being treated, the bone defect is a delayed or non-union fracture or a bone defect caused by trauma, bone resection or radiotherapy, the subject is a human, and the endothelial progenitor cells are administered at least 10 days after the injury or at least two weeks after the trauma, bone resection or radiotherapy, wherein the endothelial progenitor cells are administered in a range of concentrations of $10^7$-$10^{11}$ cells per ml of the pharmaceutically acceptable carrier.

16. The method according to claim 6, wherein the range of concentrations of endothelial progenitor cells is $10^8$-$10^9$ cells per ml of the pharmaceutically acceptable carrier.

* * * * *